(12) United States Patent
Barenthin

(10) Patent No.: US 12,331,866 B2
(45) Date of Patent: Jun. 17, 2025

(54) HOSE CONNECTOR

(71) Applicant: STRATEC SE, Birkenfeld (DE)

(72) Inventor: Volker Barenthin, Birkenfeld (DE)

(73) Assignee: STRATEC SE, Birkenfeld (DE)

( * ) Notice: Subject to any disclaimer, the term of this patent is extended or adjusted under 35 U.S.C. 154(b) by 0 days.

(21) Appl. No.: 17/102,794

(22) Filed: Nov. 24, 2020

(65) Prior Publication Data

US 2021/0156501 A1 May 27, 2021

(30) Foreign Application Priority Data

Nov. 26, 2019 (LU) .......................................... 101498

(51) Int. Cl.
*F16L 37/53* (2006.01)
*B01L 3/00* (2006.01)
*F16L 15/08* (2006.01)
*F16L 37/092* (2006.01)
*F16L 47/16* (2006.01)

(52) U.S. Cl.
CPC .............. *F16L 37/53* (2013.01); *B01L 3/563* (2013.01); *F16L 15/08* (2013.01); *F16L 37/092* (2013.01); *F16L 47/16* (2013.01)

(58) Field of Classification Search
CPC ......... F16L 37/53; F16L 37/092; F16L 47/16; F16L 15/00; F16L 15/006; F16L 15/08; B01L 3/561; B01L 3/563
USPC ...................................................... 285/143.1
See application file for complete search history.

(56) References Cited

U.S. PATENT DOCUMENTS

| 1,771,949 | A |   | 7/1930  | Blanchard |
|-----------|---|---|---------|-----------|
| 3,112,127 | A | * | 11/1963 | Campbell ............. F16L 41/007 411/395 |
| 3,502,355 | A | * | 3/1970  | William, Sr. ........... F16L 41/08 285/334.4 |
| 3,627,262 | A | * | 12/1971 | Hottle ................... F16K 31/445 251/346 |
| 2013/0014757 | A1 |   | 1/2013 | McPhearson |
| 2018/0128405 | A1 |   | 5/2018 | Brown et al. |
| 2019/0128460 | A1 |   | 5/2019 | Fremont |

FOREIGN PATENT DOCUMENTS

JP          2015054092 A      3/2015

\* cited by examiner

*Primary Examiner* — James M Hewitt, II
(74) *Attorney, Agent, or Firm* — 24IP Law Group USA, PLLC; Timothy R. DeWitt

(57) ABSTRACT

A connector for a hose transferring a medium, comprising an inner part, wherein the inner part comprises at a first end a first section comprising an opening for accommodating a hose and a second section comprising a duct arranged between an inner base of the opening for the hose and a second end of the inner part that is opposite of the first end, wherein the first section has a greater outer diameter than the second section; and an outer part, wherein the outer part comprises a thread surrounding the second section and a grip surrounding the first section, wherein the outer part is fixed rotational movable around the inner part between a flange at the inner part's second end the first section with the greater outer diameter.

14 Claims, 3 Drawing Sheets

HOSE CONNECTOR

CROSS-REFERENCE TO RELATED APPLICATION

The present application claims priority to Luxembourg Patent Application No. LU 101498 filed on Nov. 26, 2019. The aforementioned application is hereby incorporated by reference in its entirety.

BACKGROUND OF THE INVENTION

Field of the Invention

The invention relates to a hose connection for tubes of automated analyser systems transferring mediums like liquid fluids.

Brief Description of the Related Art

Automated analyser systems for use in clinical diagnostics and life sciences are produced by a number of companies. For example, STRATEC® SE, Birkenfeld, Germany, produces a number of devices for specimen handling and detection for use in automated analyser systems and other laboratory instrumentation.

The most common manner for connecting hoses that transfer liquids are screw couplings. The parts which are connect are usually made of fluoropolymers such as PTFE or FEP, in particular in the field of analysis and medical technology. Such materials provide media resistance and pressure resistance. Due to their strong creep behavior and their relatively high hardness, these hoses cannot simply be put together for connection. Special fitting screws are used for such couplings.

A tube's or hose's end is reshaped, or a flange is formed at its end using heat and pressure in order to obtain a sealed connection between the fitting and its counterpart. Such a molded flange seals between the front of the fitting and the threat root of the counterpart. A ring may be arranged between flange and fitting for uncoupling torsion forces that may occur during tightening of fitting and its counterpart.

A disadvantage of this method is that the process of flange forming requires a number of auxiliary devices or tools. On the one hand, a holding device for the hose is needed and on the other hand the actual forming tool. Often, a heated mandrel is used, which heats the tube before forming. In addition, just with this type of screw often chipped items made of materials such as PEEK are used. Especially the assembly and the parts production make this type of connection costly. In addition, the forming of such a hose connection requires some experience in the assembly and is therefore not too user friendly. The method applies only to the hard fluoropolymer tubing. Thermoplastic elastomers cannot be reshaped to the required precision due to their elasticity and lower Shore hardness.

An alternative to reshaping the end of a tube or hose is an insert that is a gasket with a cylindric hose connection and a ring for rotational decoupling. For mounting, the fitting screw is pushed over the tube or hose followed by the ring and finally, the insert is introduced into the tube or hose.

Comparable to the connection with the formed hose, often pure machined small parts made of high-quality plastics can be used in this process. The sealing flange consists of a disc with a dome. This dome is inserted with slight excess in the hose. Due to the high hardness of the hose and the small size of the components, this results in an increased effort in the assembly. By inserting the dome in the hose whose cross-section is reduced which results in a flow resistance in the system. Depending on the flow rate, the fluid is compressed in front of the dome and undergoes an expansion behind the cross-sectional reduction, which can lead to undesired turbulence.

Another possibility for sealing is to use an elastomer seal that is put over the tube's end, so that sealing takes place at the outside of the tube. In this variant, the tightness to the hose and the actual sealing seat in the counterpart is made only by an elastomeric element. Just the tightness to the counterpart is thus always dependent on the installation. If the sealing part is pushed too far onto the hose, there is no connection between the elastomer and the counterpart. The tightness is therefore no longer present. The assembly is difficult on the one hand due to the specified tolerance problem and on the other hand because of the required assembly forces. It is recommended to use a mounting device. This increases the effort and thus the costs. As with the aforementioned methods, this connection technique is limited to the rather hard fluoropolymer hoses. Sliding the connector onto softer hoses would reduce its cross section. In addition, it is questionable whether the seal part can ever postpone due to the higher friction values.

A very simple method for connecting tubes with a Shore hardness below 85 A is the use of a so-called barb connector, where the tube is put over a mandrel with a greater outer diameter than the inner diameter of the tube. In order to provide a secure connection, the mandrel shall be mushroom-shaped. This is the most common, tool-free way of connecting hoses. It is widely used when it comes to fluid transport in the low-pressure range. The hose is only put over the counterpart. The resulting, in places multiple line contact between fitting and hose guarantees the seal between the two partners. However, just this slipping also has some disadvantages. On the one hand, depending on the hardness of the hose and the selected excess between fitting and hose, the assembly is difficult. With increasing excess or increasing hardness, the contact forces, which are usually applied manually, increase sharply. To counteract, the excess can be reduced with increasing the hose hardness or wall thickness. As the excess decreases, however, the compressive strength of the overall connection also decreases. For pressure applications and the use of highly pulsating pumps, this connection may have an undefined instability. The fitting will be screwed into a counterpart. If the hose is connected to the fitting prior to screwing the fitting into its counterpart, the connection may loosen due to tensions in the hoses resulting from twisting them.

For a quick connection and release a so-called Luer lock is very often used in medical devices. Such a connection is based on two coupling pieces which are connected and sealed only by a self-locking cone. In the Lock variant results from an external thread, which can be closed by a 90°—rotation, an additional closure of a pulling apart of the conical connection and thus prevents leaks. A disadvantage of a Luer lock is that the partners of the lock are twisted against each other with the result that the hose is twisted in its elastic range. Under certain circumstances, this can mean that the connection loosens itself due to the elasticity of the hose and that leaks can occur.

In order to prevent just that twisting of the hose, this can be biased by a 90° rotation against the closing direction of the thread. This has the advantage that the hose is tension-free when the clutch is closed. However, this biasing requires an attentive user, the error rate is accordingly high. To counteract this problem, there is a rotation-coupled variant. In this case, the locking thread is loosely connected as an additional union nut with the actual Luer cone. If the clutch is now closed, the counterpart can only be recognized, by tightening the torsional coupled cap nut of the actual cone, which is connected to the hose is pressed without rotation into the cone of the counterpart.

The locking thread of the Luer Lock coupling is designed for an ergonomically comfortable ¼ turn. In order to realize a way in these only 90° rotation angle sufficient to connect the coupling partner of lots to hard a fairly large pitch is required. This large thread pitch reduces the self-locking of the thread to a significantly low level. This has the consequence that this locking thread reliably locked only with a firmly connected Luer cone and this lock also holds. In the described rotationally coupled variant, the friction of the Luer cones is eliminated. The torsional coupled union nut can only jam due to the adhesion between the screw and nut threads (self-locking). However, since this is reduced by the large pitch there is always the risk of an independent release of the locking thread. In this case, the holding force consists only of the two inserted Luer cone. Thus, with dynamically loaded systems, oscillating or vibrating connections as well as connections which are subject to strong temperature changes, this type of coupling can very quickly lead to errors.

Published U.S. Patent Application No. US 2018/0128405 A1 relates to a single action push to connect fitting for a conduit such as tube or pipe. The fitting includes a first fitting component and a second fitting component that are joined or assembled together to form a fitting assembly. The fitting assembly includes a conduit seal device and a conduit retaining device. A conduit may be manually or otherwise inserted into the assembled fitting assembly with a single axial movement and be retained and sealed without the need for further action or movement of the fitting components. A disadvantage of a fitting assembly according to this publication is that it comprises multiple parts making its assembly complex.

Published U.S. Patent Application No. US 2019/0128460 A1 relates to a tube end form, including, a first section including a first radially outward facing surface, and a shoulder axially arranged between the first and second sections, the shoulder including a first frusto-conical surface arranged at a first angle relative to the first radially outward facing surface, and a second frusto-conical surface arranged at a second angle relative to the first radially outward facing surface. This document does not relate to a connector suitable for accommodating a hose for its fixation in the connector.

SUMMARY OF THE INVENTION

It is therefore the object of this invention to provide a stable and pressure resistant hose connection.

The present invention provides a connector for a hose transferring a medium, consisting of an inner part, wherein the inner part comprises at a first end a first section comprising an opening for accommodating a hose and a second section comprising a duct which is arranged between an inner base ground of the opening for accommodating the hose and a second end of the inner part that is opposite of the first end, wherein the first section has a greater outer diameter than the second section; and an outer part, wherein the outer part comprises a thread surrounding the second section and a grip surrounding the first section, wherein the outer part is fixed rotationally movable around the inner part. The outer part may be fixed between a flange at the inner part's second end (second section) and a diameter transition area to the inner part's first section with the greater outer diameter. The outer diameter of the inner part's second section is smaller than the outer diameter of the inner part's first section.

In a further aspect of the invention, the inner diameter of the opening for the hose may conically reduce towards the inner base of the opening for the hose It is further intended that the inner part is made of a transparent material.

In a further embodiment of a connector according to the invention, the outer parts grip may provide at its end adjacent or next to the thread a surface for accommodating a marker. The surface for accommodating a marker may surround the outer part.

With respect to the inner diameter of the opening for the hose it may be identical or smaller than the outer diameter of the hose that is accommodated in the opening.

In a further aspect of the invention, the connector's outer part may have a ¼-28UNF thread.

In a further embodiment of the present invention, the inner part may be inserted into the outer part.

Another object of the invention is a first system comprising a connector as described above and a hose. It is further intended with respect to the first system that a hose may be accommodated in the opening of the inner part, e.g. the inner diameter of the opening for accommodating the hose is identical or smaller than the outer diameter of the hose that is accommodated in the opening or with an adhesive between outer diameter of the hose and inner diameter of the opening for the hose.

It is intended that hoses with an outer diameter of up to 7 mm can be accommodated into the inner part's opening for the hose.

Another object of the present invention is a second system comprising a first system as described above and a counterpart for the connector's part thread having a female thread corresponding to the thread of the connector's outer part.

Another object of the present invention is the use of a connector as described above or a first or second system as described above for connecting a hose. The connection may be to another hose or to a solid counterpart having a female thread.

Still other aspects, features, and advantages of the present invention are readily apparent from the following detailed description, simply by illustrating preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description or may be learned by practice of the invention.

BRIEF DESCRIPTION OF THE FIGURES

The invention will be described based on figures. It will be understood that the embodiments and aspects of the invention described in the figures are only examples and do not limit the protective scope of the claims in any way. The invention is defined by the claims and their equivalents. It will be understood that features of one aspect or embodiment of the invention can be combined with a feature of a different aspect or aspects of other embodiments of the invention, in which:

DETAILED DESCRIPTION OF THE INVENTION

Figure 1:
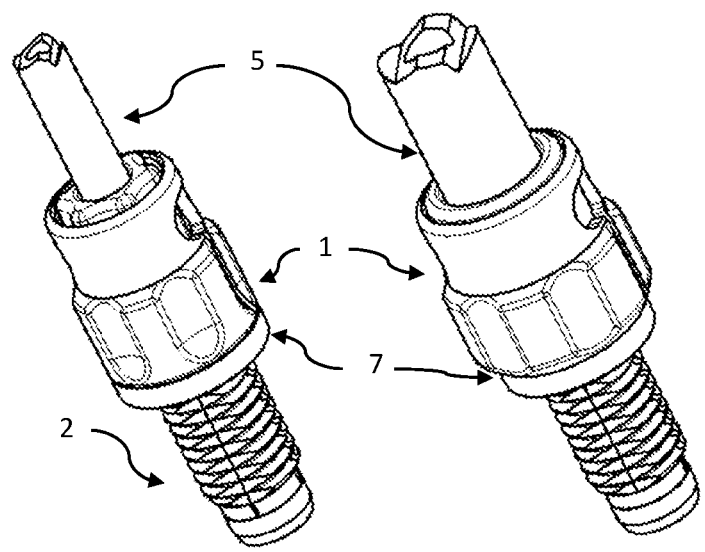
FIG. 1 shows hoses which are connected to a fitting according to the invention.

The technical problem is solved by the independent claims. The dependent claims cover further specific embodiments of the invention.

The term "inner base ground" as used herein refers to an inner surface of the inner part against which the end of a hose is pressed. The inner base ground is thus the difference in diameter between the diameter of the opening for accommodating a hose in a first section of the inner part and the diameter of the duct in a second section of the inner part.

The outer part is fixed around the inner part in a manner that the outer part can be rotated around the inner part. Thus, the outer part is fixed rotationally movable around a longitudinal axis around the inner part. The outer part may be fixed between a flange located at the inner part's second end (end of second section) and a diameter transition area to the larger diameter of the first section.

The term "medium" shall refer within the meaning of the present invention to be a liquid comprising solid parts like particles of any material and of biological or synthetic origin or a gas comprising liquid droplets and/or solid particles.

A "marker" within the meaning of the present invention refers to elements that may be used to label a connector so that it can be differentiated from other connectors. A marker can be a ring or an adhesive comprising a specific color or any barcode. An RFID tag may also be a marker according to the present invention.

The present invention refers to a two-part, torsional coupled fitting within the meaning of a fitting screw for female thread (e.g., ¼-28UNF) in which thermoplastic elastomer hoses with an outer diameter of up to 7 mm can be glued without the need of additional components such as a flange that has to be attached to the hose's end to achieve tightness.

The inner part of the torsional coupled fitting generates a sealing connection between the hose and the counterpart. The hose is merely joined with a solvent adhesive cohesively into the inner part. The sealing connection results from pressing the end face of the inner part against the thread root of the counterpart.

The outer part establishes the mechanical connection between the inner part and the counterpart. Here, the inner part is anchored in the outer part. This is done by plugging the inner part and outer part together and then anchoring both components. The outer part may have a thread (e.g., ¼-28UNF) and provides the necessary mechanical contact force or pressure to the inner part and is thus responsible for the contact force or pressure of the inner part to the end face of the thread root of the counterpart. This combination of bonding techniques enables the transfer of pressures comparable to those of classic joints (e.g., ¼-28UNF).

The inner part and outer part are merely inserted into each other translationally only along a z-axis, a rotational movement about the z-axis is remaining. This allows rotational decoupling between hose and screwed outer part. The hose that is cohesively connected to the inner part can be connected to the nut thread without twisting it.

The thread (e.g., ¼-28UNF) has a comparatively low pitch regarding the locking thread of a Luer lock connection. Usually, fittings with threads (e.g., ¼-28UNF) require between 5 and 9 turns to establish a reliable connection between two coupling partners. The resulting self-locking between screw and nut thread is significantly higher compared to the locking thread of the Luer lock connection. As a result, these connections remain permanently sealed even with vibrations and temperature changes.

Very thin walls can be realized in both components by using specific plastics. If the fitting is completely mounted and screwed in addition, the circumferential nut thread additionally supports the connection. This makes it possible to realize internal cross sections of up to 3.2 mm in the fitting. This means that hoses can be connected to the inner diameter of 3.2 mm within the respective fitting, without the need of significantly reducing the inner diameter and thus affecting the flow rate.

Using transparent plastics allows for visual inspection and assessment of the joining process between the hose and the inner part of the connector. Defective connections can thus be identified quite easy even before fitting the fitting parts.

The present invention allows connection of thermoplastic elastomer hoses in a very small space with other systems. The connection does not significantly reduce the cross-section of the hose line. In addition, the connection is pre-stressed via the thread (e.g., ¼-28UNF) and is therefore pressure-resistant and protected against loosening by itself.

A connection according to the present invention shall fulfill the following requirements:

Pressure-resistant up to min. 8bard;
Low cost structure;
Simple installation;
Resistant to vibration;
Suitable for thermoplastic elastomers such as PVC or TPU as tubing;
No or no significant reduction in cross-section flow;
Connection through a thread, e.g., ¼-28UNF;
Optical assignment of several hoses; and
Tolerant of incorrectly executed hose cuts (angularity, surface quality).

The embodiment shown in FIG. 1 shows hoses 5 which are connected to a fitting 1 that has a thread 2. A ring 7 is arranged at the fitting as a marker enabling to distinguish different fittings/hoses transferring different liquids.

Figure 2:
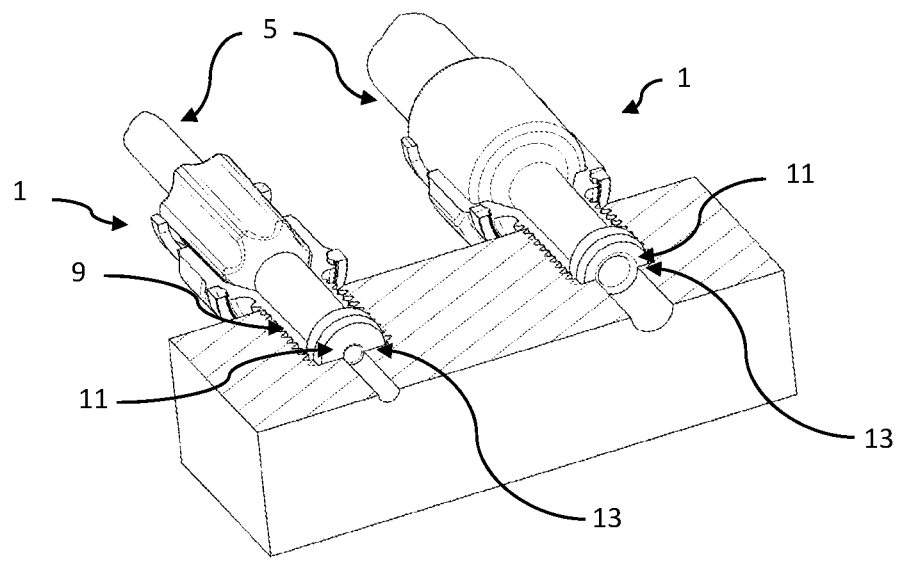
FIG. 2 shows which are interlocked in two-part torsional fittings.

The exemplary design in FIG. 2 shows hoses 5 which are interlocked in two-part torsional fittings 1. The screw connection 9 is resistant against vibrational movements and pressure. The front side 11 is pressed against the thread ground 13 so that a reliable sealing results even during pressurization.

Figure 3:
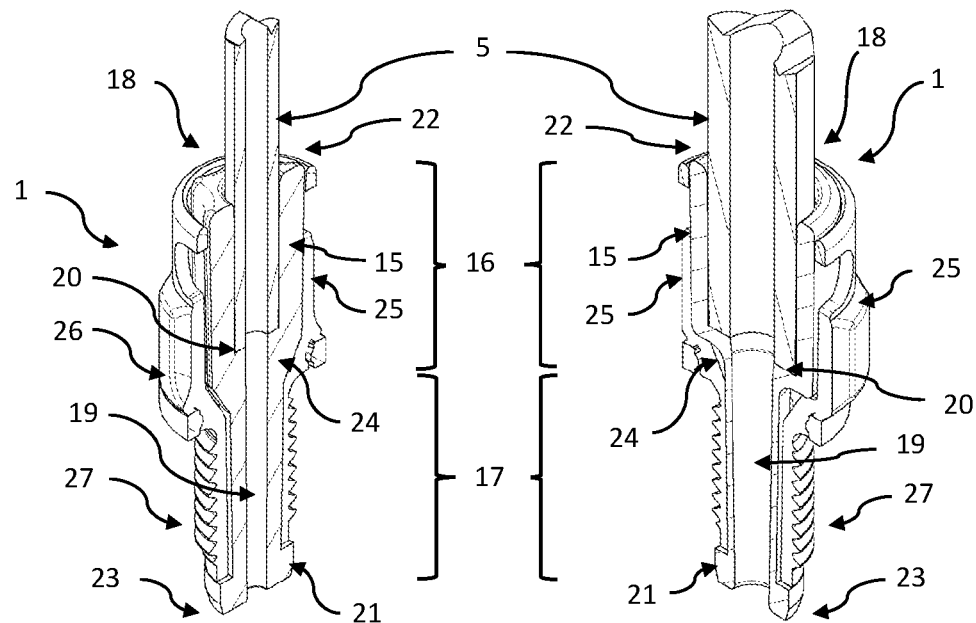
FIG. 3 shows sectional views through two-part torsional fittings according to the invention.

FIG. 3 shows sectional views of two different embodiments with hoses 5 having a different diameter, which are glued into the inner part 15 of a two-part torsional fitting 1 according to the invention. The inner part 15 of a two-part torsional fitting 1 can be transparent so that the gluing can be optically verified.

Outer part 25 surrounds inner part 15. The inner part 15 has a first section 16 between the opening for a hose 18 on a first end 22 of the inner part 15 and its base ground 20. The first section 16 further comprises a transition area 24 to the second section 17. The transition area 24 may also be part of the second section 17 or may be arranged between first and second section 16, 17. The first section 16 of inner part 15 is surrounded by a grip element 26 of outer part 25. Transition area 24 may be shaped conically (left part of FIG. 3) or in one step (right part FIG. 3).

The inner part 15 has further a second section 17 starting below transistion area 24 of the first part 15 and a second end 23 of the inner part 15. Second section 17 of inner part 15 is surrounded by a thread 27 on outer part 25.

In both embodiments shown in FIG. 3, the inner part 15 has a flange at the second end 23. Thus, outer part 25 is fixed between first section 16 of the inner part 15, which has a larger diameter than its second section 17 and flange 21.

The sectional views in FIG. 3 show further that there is no significant reduction of the inner diameter in the transition from the hose to inner part 15 of the two-part torsional fitting 1. Thus, the flow of liquids will not be influenced or impeded.

One advantage of the invention is to provide a user-friendly connection and disconnection of hose connections made of thermoplastic elastomers. The direct bonding of the hose within the fitting eliminates the need to attach the hose. The entire composite can be screwed and tightened by hand through the thread. In case of a necessary replacement, the entire composite can be unscrewed. Peeling off the tube, which may cause injuries is eliminated.

Another advantage is the lack of mechanical stress by the torsional fitting. It is not possible to twist or torsional stress the hose during screwing due to the possibility of rotational decoupling. The hose can not exert any mechanical stress on the periphery regardless of the bending radii after screwing.

The two-part torsional fitting has no significant cross-sectional changes which may cause turbulences. The constant cross-section of the complete composite does not allow the formation of turbulences at cross-sectional changes, edges, heels, etc. This reduces interfering effects such as spontaneous outgassing or cavitation.

Another advantage of the present invention in this regard is that no significant cross-sectional reductions are present that may act as flow resistances. Any flow resistors are omitted.

A safe cohesive connection between hose and connector is a further advantage provided by the present invention. The material connection between the fitting and hose generates a connection which is not susceptible to mechanical effects, e.g., tensile forces, vibrations, pressure or the like. This makes the entire composite safe and reliable during application.

The present invention further provides a pressure resistant connection by pressing two sealing surfaces via screw connection on a counterpart. This type of pressure-resistant connection is also used in hydraulics, where only two sealing surfaces are pressed against each other. The necessary contact pressure is applied via a thread. A high gear reduction results from screwing because of the pitch of the thread. Thus, the sealing connection can be made only by hand. In addition, the selected slope prevents self-locking an independent release of the connection.

Finally, the possibility to visually inspect the adhesive bond by using transparent materials is an advantage, so that the cohesively produced compound can be verified immediately after bonding. Inclusions of air bubbles, use of too much or too little adhesive and damage to the fitting or hose will be immediately visible.

Alternative approaches to circumvent or realize the present invention encompass the use of currently used fluoropolymer hoses, which have the above mentioned advantages of rotational decoupling, constant flow cross-section, pressure stability etc.

Figure 4:
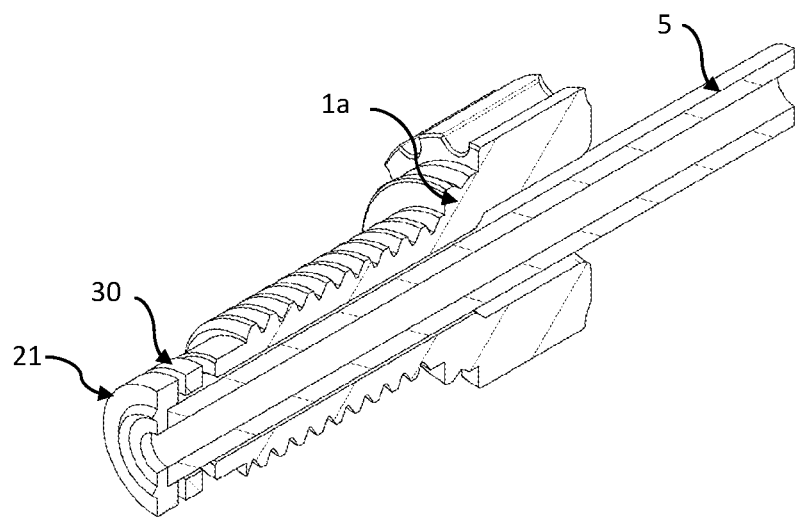
FIG. 4 shows a one-part fitting with an attached flange.

The flange 21 may also be fixed to a one part fitting 1a as a separate component (FIG. 4). One possibility to fix such a flange 21 can be to glue it to hose 5. The above described methods for reshaping the end of the hose or applying an additional part to a hose's end to generate a sealing effect between fitting screw, hose and counterpart relate mostly to fluoropolymers. Thus, materials which can not just be plugged because of their low surface energy, their creep behavior, their high hardness or their pressure resistance. Pressure-resistant hoses may also be made of materials with a higher surface energy, so that materials can be added by cohesive methods such as gluing them. Thermoplastic polyurethanes (TPU) belong to the thermoplastic elastomers, which can be treated with a suitable solvent. A flange 21 made of an appropriate material may be treated in the same way e.g. the inner surface may be dissolved with a solvent, so that both part can be connected or cold welded.

Thus, it will be possible with such an approach to apply cohesively a flange 21 made of TPU on the front side of the hose 5 made of TPU. In this case, the reshaping of the hose's end or inserting an additional part into it will be eliminated. However, it will also be required that an additional decoupling ring 30 is added for decoupling torsional forces between the fitting 1a and flange 21 when tightening the composite.

Figure 5:
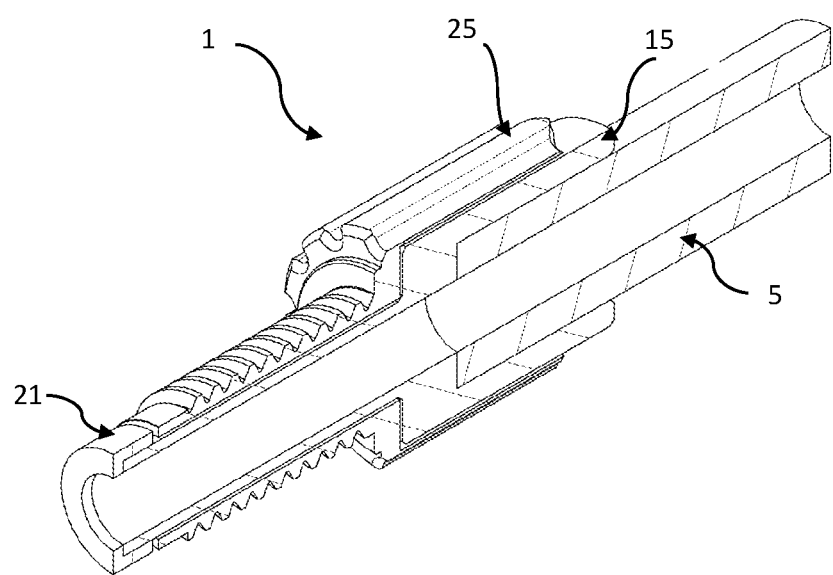
FIG. 5 shows a two-part torsional fitting with an attached flange.

The other possibility is to glue the hose 5 into the inner part 15 of the two-part torsional fitting 1, similar to the method described above. Flange 21 shown in FIG. 4 forms an undercut. Thus, the inner and outer parts (15, 25) can be mounted together only by a deformation of the outer part. This is realized over a defined elastic range of both components so that they are locked together. Alternatively, the flange 21 can be made separately. Thus, it will be possible to first insert the outer and inner parts (15, 25) into each other. Subsequently, flange 21 is glued to the front side of the inner part and thus fixes the inner and outer parts to each other (FIG. 5).

A further approach is that the inner part and hose can be connected directly in the injection molding tool instead of glueing them. The hose is inserted in the tool and overmoulded with the plastic.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

REFERENCE NUMERALS 1 two-part torsional fitting
1a one part fitting
2 thread
5 hose
7 ring
9 screw connection 11 front side
13 thread ground
inner part
16 first section
17 second section
18 opening for hose
19 duct
base ground
21 flange
22 first end
23 second end
24 diameter transition area
outer part
26 grip element
27 thread
30 decoupling ring

What is claimed is:

1. A connector configured to connect to a hose transferring a medium, comprising:
   an inner part, wherein the inner part comprises at a first end a first section comprising an opening configured to accommodate a hose and a second section comprising a duct which is arranged between an inner base ground of the opening and is configured to accommodate the hose and a second end of the inner part that is opposite of the first end, wherein the first section has a greater outer diameter than the second section; and
   an outer part surrounding the inner part, wherein the outer part comprises a thread surrounding the second section of the inner part and a grip surrounding the first section of the inner part, and wherein the outer part is fixed rotationally movable around the inner part: wherein the thread is arranged between a flange of the inner part's second end resulting from a reduced external diameter of the inner part which extends up to a diameter transition area to the larger diameter of the inner part's first section.

2. The connector of claim 1, wherein the inner diameter of the opening for the hose is conically reduced at the inner base ground of the opening for the hose.

3. The connector of claim 1, wherein the inner part is made of a transparent material.

4. The connector of claim 1, wherein the outer part's grip provides at its end adjacent to the thread a surface for accommodating a marker.

5. The connector of claim 4, wherein the surface for accommodating a marker surrounds the outer part.

6. The connector of claim 1, wherein the outer part has a ¼-28UNF thread.

7. The connector of claim 1, wherein the inner part is inserted into the outer part.

8. A system comprising:
   a connector configured for a hose transferring a medium, consisting of:
      an inner part, wherein the inner part comprises at a first end a first section comprising an opening configured for accommodating a hose and a second section comprising a duct which is arranged between an inner base ground of the opening configured for accommodating the hose and a second end of the inner part that is opposite of the first end, wherein the first section has a greater outer diameter than the second section; and
      an outer part surrounding the inner part, wherein the outer part comprises a thread surrounding the second section of the inner part and a grip surrounding the first section of the inner part, and wherein the outer part is fixed rotationally movable around the inner part: wherein the thread is arranged between a flange of the inner part's second end resulting from a reduced external diameter of the inner part which extends up to a diameter transition area to the larger diameter of the inner part's first section.

9. The system of claim 8, wherein the inner diameter of the duct is identical to the inner diameter of the hose.

10. The system of claim 8, wherein the inner diameter of the opening for accommodating the hose is identical or smaller than the outer diameter of the hose that is accommodated in the opening.

11. The system of claim 8, wherein a hose is accommodated in the opening of the inner part with an adhesive between outer diameter of the hose and inner diameter of the opening for the hose.

12. The system of claim 8, wherein a hose with an outer diameter of up to 7 mm is accommodated in the inner part's opening for the hose.

13. The system of claim 8 further comprising:
   a counterpart for the connector's outer part thread having a female thread corresponding to the thread of the connector's outer part.

14. A method of using a system according to claim 8 comprising the step of connecting a hose in the connector.

* * * * *